United States Patent [19]

Brackin

[11] Patent Number: Plant 7,555

[45] Date of Patent: Jun. 11, 1991

[54] WAX MYRTLE NAMED LANE

[76] Inventor: Randall L. Brackin, P.O. Box 2127, Selma, Ala. 36701

[21] Appl. No.: 451,981

[22] Filed: Dec. 18, 1989

[51] Int. Cl.[5] ..... A01H 5/00

[52] U.S. Cl. ..... Plt./51

[58] Field of Search ..... Plt./51, 54

*Primary Examiner*—Howard J. Locker

*Attorney, Agent, or Firm*—Jennings, Carter, Thompson & Veal

[57] ABSTRACT

A new variety of Wax Myrtle distinguished by its deeply serrated leaf pattern and its resistance to leaf spot disease as well as the characteristic wax myrtle fragrance when crushed.

5 Drawing Sheets

BACKGROUND OF THE NEW PLANT

This new Wax Myrtle variety originated from unknown parentage growing among a group of wax myrtles maintained at a nursery at Selma, Ala., this plant having been discovered by me in 1982 and selected for propagation and test because of its unusual leaf pattern and apparent resistance to leaf spot disease. Asexual reproduction of this plant was done by means of cuttings at Selma, Ala., and after further propagation through successive generations, it was determined that not only did the new plant have excellent horticultural characteristics for the commercial market but also that its novel characteristics have been determined to be firmly fixed and hold true from generation to generation. That is, the unusual leaf pattern and apparent resistance to leaf spot disease hold true from generation to generation.

DESCRIPTION OF THE DRAWINGS

This new wax myrtle plant is illustrated by the accompanying drawings, of which Sheet 1 is a photographic view of a mature plant grown in full sunlight in a private nursery in Selma, Ala., showing the general form and arrangement of the plant;

Sheet 2 is a photographic view of branch of plant grown in a greenhouse showing the unusual leaf pattern from upper side of the leaf;

Sheet 3 is a photographic view of a branch of a plant grown in a greenhouse showing the underside of the leaf, and Sheets 4 and 5 are prints of machine copies of the front and back sides, respectively, of typical leaves of this plant.

DESCRIPTION OF THE NEW PLANT

The following is a detailed description of the new plant based on observations made in a greenhouse and in a nursery in Selma, Ala. The color designation being according to The R.H.S. Colour Chart published by The Royal Horticultural Society of London, England.

The Plant

Origin: Unknown.

Parentage: Unknown.

Classification:

*Botanic.*—*Myricia cerifera.*

*Commercial.*—Wax Myrtle.

Form: Shrub-like, with a height to about 12 feet and a diameter to about 8 feet.

Foliage:

*Quantity.*—Abundant, with distinct wax myrtle fragrance when crushed.

*Size of leaf.*—Width — from about one-tenth to about one-half inch. Length — About four to six inches.

*Shape.*—Elongated with deep serrations on each side of the leaf with the serrations being generally paired and having a length from the crest to the bottom of each serration which is generally longer than the width of the serration such that the serrations are substantially triangular, the leaf being broadest at about ⅔ its length from the stem.

*Texture.*—Smooth.

*Color.*—Upperside —137A non-glossy granulated dark green; Underside — 137C granulated flat green.

*Ribs and veins.*—A yellow green Midrib, 147C, runs midline from tip of the leaf to the base on both upper and lower sides.

*Bark.*—Branches are grey-green 197A with yellow-white 158A stippling. New leaf stem branches are grey-brown 199A with white stippling.

The plant is tolerant to full sunlight and shade, and has shown no damage at temperatures of as low as −4 degrees Fahrenheit.

The plant has not been observed to have any buds or fruits or to exhibit any sexual characteristics. The coloration of the plant is the same as the common wax myrtle, with the leaves taking a slightly amber shade when the plant is grown in full sunlight. This new wax myrtle plant is particularly distinguished by its deeply serrated shape of the leaf and the absence of leaf spot disease.

I claim:

1. A new and distinct Wax Myrtle cultivar, substantially as herein shown and described, distinguished by its deeply serrated leaf shape a yellow-green mid-rib and resistance to leaf spot disease.

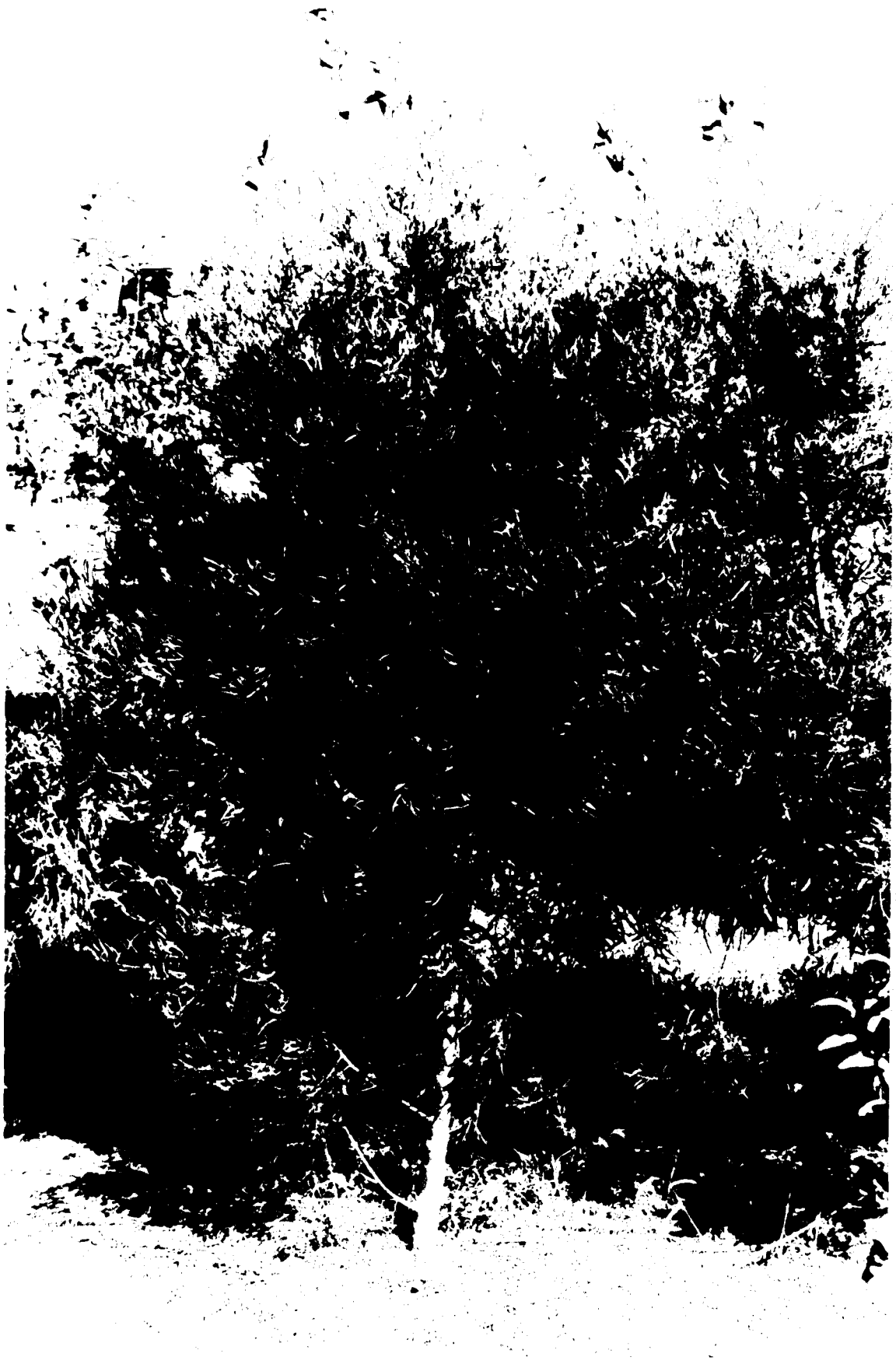

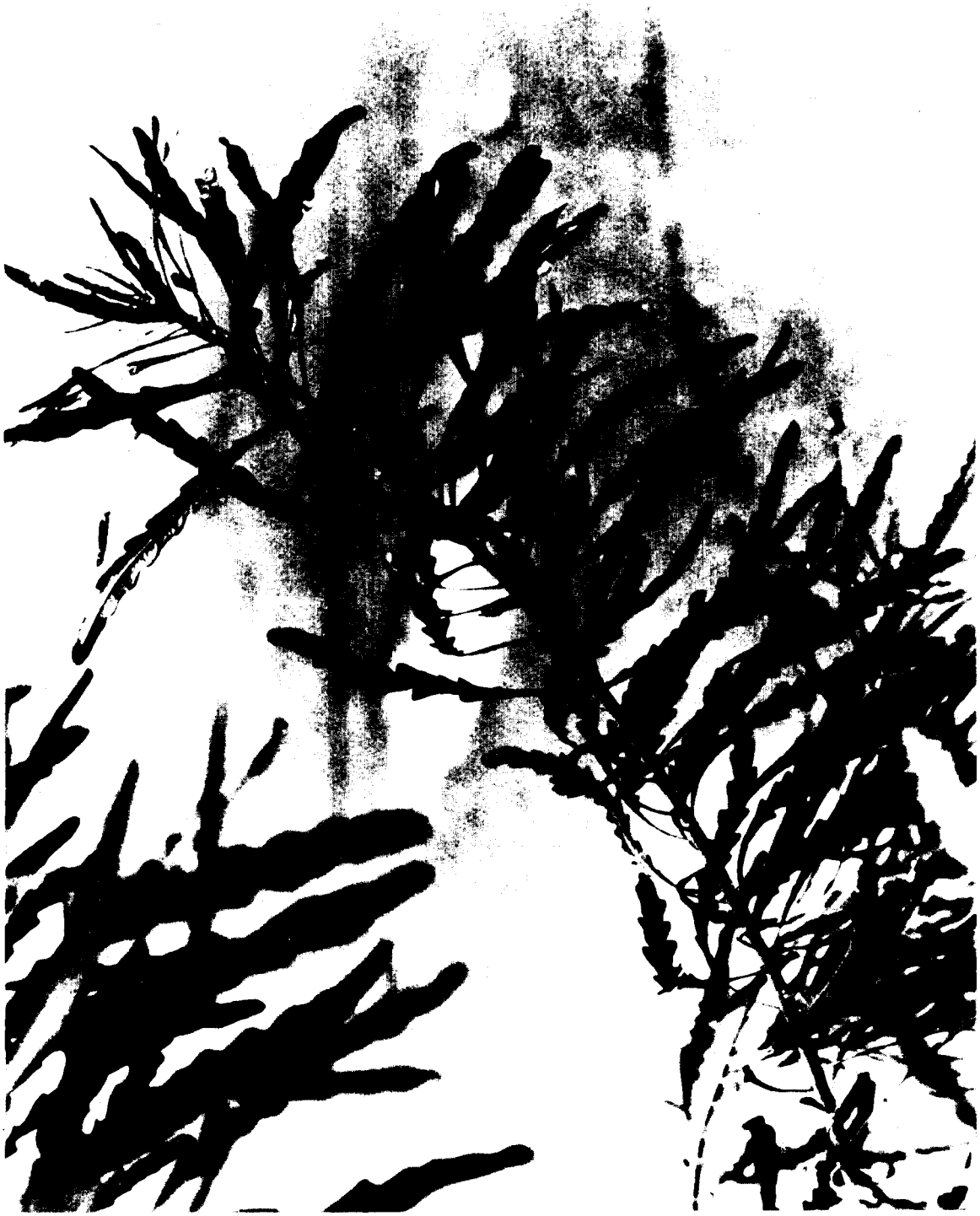

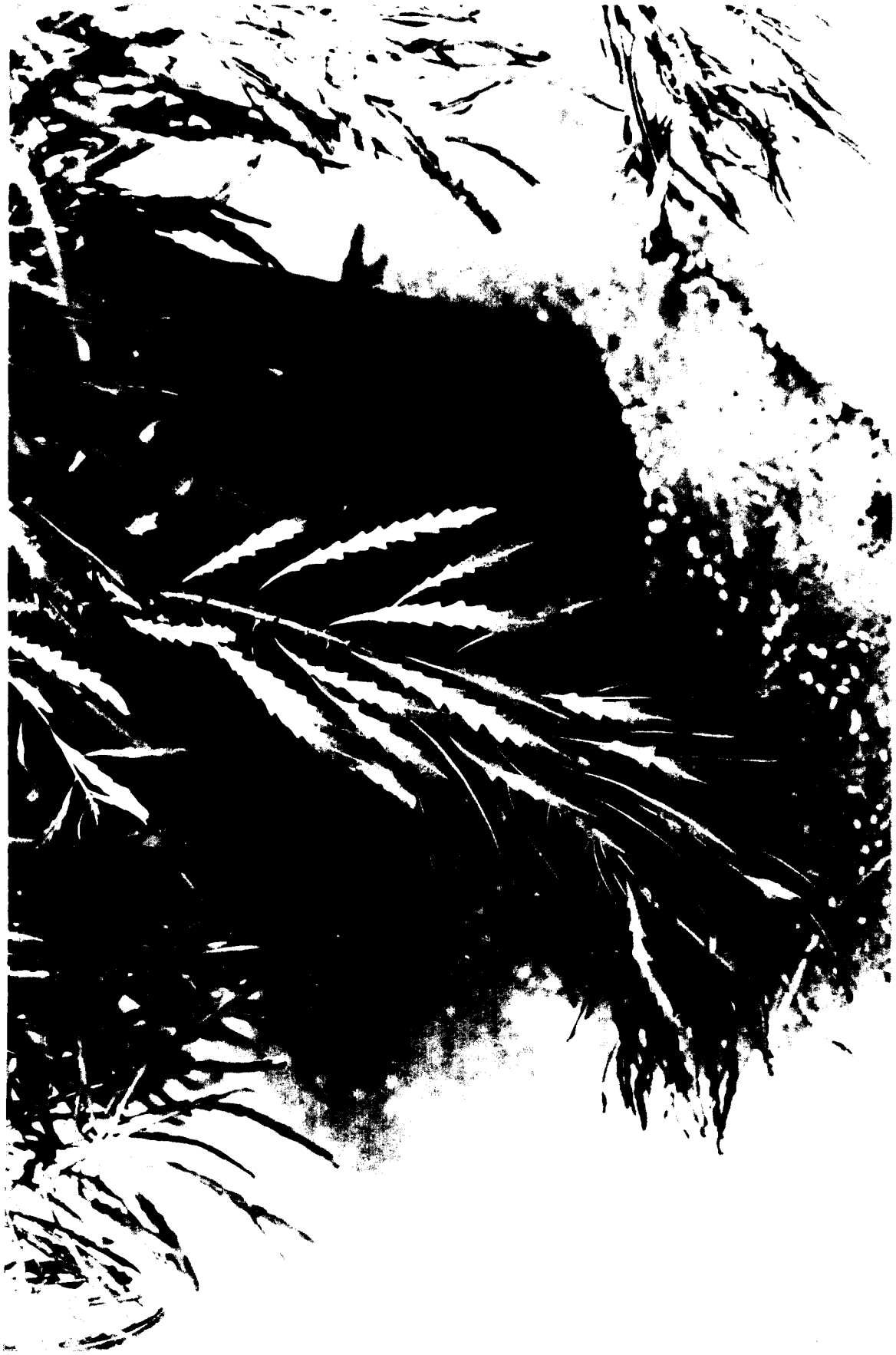

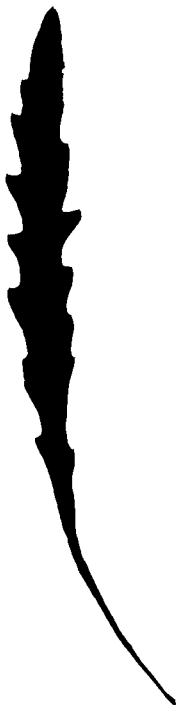

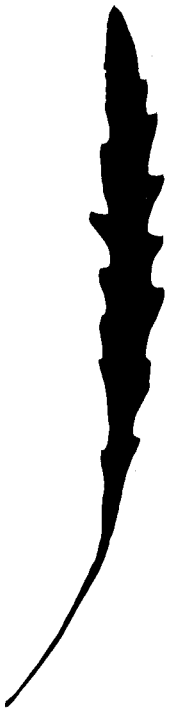

* * * * *